United States Patent [19]
Whiting-O'Keefe

[11] Patent Number: 6,061,657
[45] Date of Patent: May 9, 2000

[54] TECHNIQUES FOR ESTIMATING CHARGES OF DELIVERING HEALTHCARE SERVICES THAT TAKE COMPLICATING FACTORS INTO ACCOUNT

[75] Inventor: Quinn Whiting-O'Keefe, Redwood City, Calif.

[73] Assignee: Iameter, Incorporated, San Mateo, Calif.

[21] Appl. No.: 09/025,321

[22] Filed: Feb. 18, 1998

[51] Int. Cl.[7] .................................................. G06F 159/00
[52] U.S. Cl. ............................ 705/2; 705/3; 705/34; 702/179
[58] Field of Search ..................... 705/10, 1, 8, 2–4, 705/34; 706/924, 923; 702/179

[56] References Cited

U.S. PATENT DOCUMENTS

| | | | |
|---|---|---|---|
| 4,667,292 | 5/1987 | Mohlenbrock et al. | 705/2 |
| 4,957,115 | 9/1990 | Selker | 600/509 |
| 5,018,067 | 5/1991 | Mohlenbrock et al. | 600/300 |
| 5,099,424 | 3/1992 | Schneiderman | 705/3 |
| 5,136,502 | 8/1992 | Van Remortel et al. | 705/2 |
| 5,225,976 | 7/1993 | Tawil | 705/2 |
| 5,253,164 | 10/1993 | Holloway et al. | 705/2 |
| 5,301,105 | 4/1994 | Cummings, Jr. | 705/2 |
| 5,307,262 | 4/1994 | Ertel | 705/2 |
| 5,324,077 | 6/1994 | Kessler et al. | 283/54 |
| 5,325,293 | 6/1994 | Dorne | 705/2 |
| 5,359,509 | 10/1994 | Little et al. | 705/2 |
| 5,420,786 | 5/1995 | Felthauser et al. | 705/2 |
| 5,524,645 | 6/1996 | Wills | 128/898 |
| 5,544,044 | 8/1996 | Leatherman | 705/3 |
| 5,557,514 | 9/1996 | Seare et al. | 705/2 |
| 5,639,623 | 6/1997 | Yamauchi | 435/7.24 |
| 5,652,842 | 7/1997 | Siegrist, Jr. et al. | 705/2 |
| 5,666,492 | 9/1997 | Rhodes et al. | 705/3 |
| 5,715,835 | 2/1998 | Lishko et al. | 128/898 |
| 5,781,442 | 7/1998 | Engleson et al. | 364/478.02 |
| 5,781,893 | 7/1998 | Felthauser et al. | 705/10 |
| 5,798,267 | 8/1998 | Harasymiw | 436/97 |
| 5,835,897 | 11/1998 | Dang | 705/2 |
| 5,842,173 | 11/1998 | Strum et al. | 705/1 |

*Primary Examiner*—James P. Trammell
*Assistant Examiner*—Cuong H. Nguyen
*Attorney, Agent, or Firm*—Majestic, Parsons, Siebert & Hsue

[57] ABSTRACT

The expected charges for treating a patient are estimated by the use of linear regression techniques wherein variables and coefficients of estimate models are built from historic patient data of all episode types (inpatient, office visits, etc.) and which include secondary and collateral illnesses that greatly affect the cost of treating a patient for the primary illness. In addition to evaluating the primary illness, the evaluation of collateral illness is also made possible since the processing techniques are not simply averaging data for the primary illness as has been done in the past. This allows physicians to understand the magnitude and types of resource usage that are appropriate for particular illnesses. The present invention allows better management of many aspects of the healthcare system by significantly reducing a component of the difference between the estimate and actual charges for treating a particular illness of a patient that is due to the general state of health of the patient. This then allows the remaining difference to be attributed to differences in the way that health service providers treat each illness of a patient. Estimates are made for the expected cost of providing specific episodes of care, to treat each illness in its entirety by use of both in-patient and out-patient services, and to provide the specific procedures used for the appropriate management of each illness of each patient.

31 Claims, 6 Drawing Sheets

Microfiche Appendix Included
(1 Microfiche, 53 Pages)

TECHNIQUES FOR ESTIMATING CHARGES OF DELIVERING HEALTHCARE SERVICES THAT TAKE COMPLICATING FACTORS INTO ACCOUNT

REFERENCE TO A MICROFICHE APPENDIX

An Appendix in the form of 1 microfiche containing a total of 53 frames forms a part of the disclosure herein.

BACKGROUND OF THE INVENTION

This invention relates generally to the management of a healthcare system, and, more specifically, to techniques for estimating charges for treating patients with defined primary and collateral illnesses.

There have been several statistical techniques proposed or implemented that have a goal of homogeneously grouping encounters of patients within the healthcare system by some measure of the outcome of the encounter, such as by the length of stay in a hospital or charges of the healthcare provider to render the healthcare services. Most of this effort has been directed to analyzing the resource consumption of in-patient (hospital) stays. Common to these systems is the categorization of each instance of the delivery of healthcare services into one of a large number, usually hundreds, of categories of illnesses and/or treatments. It is desired that the charges of all services in a given category be quite close to each other in order that an average of such charges can be used as a measure of what all services falling within that category should cost. That is, for example, when a patient is treated for one condition, such as congestive heart failure, an average of all charges for other patients treated for the same condition is taken as a measure of what the charges should be to treat this specific patient.

The United States government uses such a system of 470+ Diagnosis Related Groups ("DRGs") to reimburse healthcare providers under Medicare for hospital admissions. Many illnesses are defined by multiple DRGs that differ by an age range of the patient or whether there exists a co-morbidity or complication along with the principal diagnosis (the diagnosis which occasioned the admission). But this one separate category for the existence of any co-morbidity or complication does not take into account the large differences in the complexities of illnesses that can result among the large number of secondary or collateral conditions that are possible with any given primary illness. Health providers code diagnoses and procedures performed by use of the International Classification of Diseases—9th Revision, Clinical Modification ("ICD-9-CM"), approximately 15,000 different codes being in use. Each such code is grouped into individual ones of the DRG's, and a reimbursement amount associated with that DRG is then paid to the hospital or other health provider, no matter how more expensive than normal the treatment may be because of extraordinary secondary illnesses and the like.

It has long been recognized that there is a significant variation in the cost to treat patients within one category, so that the average is not a good predictor of what the charges for treating any particular patient will or should be. Therefore, there has been a significant effort to select categories and/or increase the number of categories to improve the homogeneity of the charges within each category. It has been thought that this is the way to obtain average charges that can be reliably used to estimate what the charges should be for the purpose of reimbursing the healthcare provider or determining expected charges that can be used to evaluate the efficiency of the healthcare provider. But such techniques have not sufficiently reduced the variation of charges in individual categories to bring about this result. It is not known what portion of the variations are due to differences in the level of illness of the patients and what is caused by differences in the efficiency or style of the healthcare providers. It is the efficiency of the healthcare providers that is desired to be quantified in order to manage them within a healthcare system.

A large body of medical literature documents that patients who are older, have more serious and complex illnesses which extend across multiple body systems (heart, lungs, etc.) are at greater risk of exhibiting higher mortalities, having poorer health and functional status, and consuming greater resources. Therefore, it is a principal object of the present invention to provide a technique of analyzing patients' health data that improves the ability to compare the performance of healthcare providers by significantly reducing variations between expected and actual outcomes (such as charges) due to differences in clinical complexity (severity of illness, and the existence and severity of co-morbid status) among the patients.

It is another principal object of the present invention to provide a technique for improving the accuracy of estimating likely charges (expenditure of resources) for treating a given patient.

It is a further object of the present invention to provide a technique for estimating the financial burden of each illness within each patient in such a way as to allow independent assessments of each illness.

SUMMARY OF THE INVENTION

These and additional objects are accomplished by the present invention, wherein a significant departure has been made in the continuing efforts by others to redefine the categories of illnesses in order to improve their homogeneity. Briefly and generally, the present invention takes a much different approach by applying techniques of regression analysis in particular ways to significantly reduce variations in estimated outcomes of treatment that are caused by the large variation in the level of overall clinical complexities of patients that are being treated for the same primary illnesses and collateral illnesses. Estimates of charges for such treatment are made by quantitatively including the effects of any other illnesses or complicating factors that are revealed by the input data to be specific to a given patient. This significantly reduces patient variability as a cause of differing charges to treat different patients for the same illness. Remaining differences are then primarily the result of differences among health providers, thus allowing their performance to be objectively evaluated and improved.

According to the present invention, a mathematical estimate model is built for each of a list of defined primary illnesses. The outcome of expected charges is expressed as a function of model variables and regression coefficients taken or derivable from data within historic records of patient encounters with health providers. The data upon which the variables and coefficients are dependent include data of secondary illnesses and other complicating factors that affect the charges which are a surrogate for medical resources consumed by the diagnostic and treatment processes ordered by physicians and other care givers. A set of regression coefficients is calculated by applying the mathematical model to a historic database of health encounter records of a large population of patients. These regression coefficients are stored in a table. An estimate of charges is then made for an individual patient or group of patients by reading from this table the applicable coefficients and using them in the same mathematical model as was used to calculate the coefficients but now with the new patient data.

Since these coefficients and the estimate model include the effect of the specific secondary and collateral illnesses and other complicating factors in the large population database, the estimate takes into account the specific health conditions of the patient or group of patients that can affect the amount of resources which will be expended to treat the primary illness. This is much more accurate than merely averaging the charges for all patients having the same primary illness, as has been done before, even when two or more categories of the primary illness are maintained according to the complicating or co-morbid conditions, as is done with the DRG and other software groupers. According to the present invention, estimates are made directly from the data without going through some intermediate classification based upon clinical complexity (such as illness severity).

The present invention also provides the ability to analyze secondary (complicating) and collateral (co-morbid) illnesses independent of all other illnesses. This allows physicians to understand which illness and its diagnosis and treatment resource utilization accounts for more or less of the observed charges (spending). This is not possible in a system which uses averaging and thereby loses the specificity of each illness and its incremental impact on the observed total charges or resources consumed.

According to one specific aspect of the present invention, the regression analysis is performed in two or more stages using the estimates resulting from a previous stage as independent variables in one or more subsequent stages, both when calculating the set of regression coefficients and when using them to make an estimate for a specific patient or group of patients. That is, two or more estimate models are used, the first providing a rough estimate of charges which is then used as a variable of the second model. This technique reduces the number of quantities in each of the two or more mathematical models, which makes the processing more manageable.

According to another specific aspect of the present invention, two or more similar but different mathematical models are used in each estimate stage. One model uses all the variables believed to provide the best estimate for that stage but in case there is not enough data of all those variables, one or more additional models are provided with fewer variables or variables based upon patient data that is more likely to occur for most of the primary illnesses.

The foregoing inventive processing and charge estimating techniques are useful with in-patient data alone, some specific set of out-patient data, or some sub-set of these. However, the techniques of the present invention are most useful, although not limited, to the management of healthcare systems when data of the full continuum of care is used. This allows calculating all charges expected to be incurred in connection with an illness in any care setting over time. Therefore, it is preferred to form summary records from data of records of encounters of patients with both in-patient and all types of out-patient healthcare. Estimates specific to individual patients or a group of patients are then made, according to another aspect of the present invention, for all charges related to a primary or collateral illness, or for charges related to specific components of provided services.

In a specific implementation of the present invention, patient data is maintained in four categories, generally according to the setting in which healthcare service is provided. One category is in-patient ("IP") services provided while the patient is admitted to a hospital. Another is a visit to a doctor's office ("OF"). A third category is a day encounter ("DE"), which includes one day visits to a medical facility for a procedure. The last category is therapeutic series ("TS"), which includes a closely related series of encounters such as radiation treatments, chemotherapy, and the like. Patient data is obtained from encounter records including hospital discharge forms and insurance reimbursement forms.

As an early step of the processing, the encounter records are grouped by episodes of care. Each episode is one day in length, except for extended treatments resulting from a hospitalization or a therapeutic series. One of a list of primary illnesses is identified for each episode from the data of the encounter record(s) that make(s) up the episode. Such records nearly always indicate a primary diagnosis of the patient's condition, indicating the reason for the encounter, which is the most important piece of information which is used to determine the primary illness. However, the primary illness for a given episode is determined by an algorithm that considers whether an illness that would otherwise be indicated is really a continuation or recurrence of a previous illness of the patient. Any collateral and secondary illnesses (sub-illnesses) indicated by the data are also carried as part of the episode records since this is important to estimating charges, as mentioned above. The encounter records often indicate secondary diagnoses that are used to determine such sub-illnesses but data of prior episodes can also be used.

Expected charges for an episode can be calculated by the present invention for the purpose of comparing the performance of providers of the same episode services to different patients. Such episodes are of a single type of service, such as IP, DE or TS. But it is often preferable to be able to estimate the charges to manage a patient's entire illness which usually includes several episodes of care. If an illness is chronic, such as diabetes mellitus, it has an indefinite duration and the charges are estimated per year. If an illness is acute, such as a broken arm, it has a finite duration and such a duration is assigned to each type of such occurrence. Episodes of an acute illness are then included in a particular occurrence of that illness so long as they are within the specified duration of the first episode within this occurrence. Episodes falling outside of that window usually cause the beginning of a new occurrence of the same illness. The overall efficiency of health providers in treating a chronic illness ("illness") and an acute illness ("illness occurrence") can then be compared. Other combinations can also be estimated by the present invention by limiting the types of episodes included in each illness and illness occurrence, such as using only OF and DE.

It is also often desired to be able to estimate charges for particular categories or classes of care used to treat an illness or illness occurrence. According to a further aspect of the present invention, a list of procedure classes is established, such as emergency room visits, and radiology procedures. Charges are estimated for each such procedure class for a given illness from the data maintained as part of the illness or illness occurrence records. This allows comparison among health providers as to which are using the emergency room too much or two little, or sending patients for radiology examinations too much or too little, and so forth.

Although the present invention is primarily described herein with respect to the example of estimating charges, the various aspects of the present invention are also applicable to estimating other outcomes of treatment. The length of stay in a hospital, mortality, patient satisfaction and a measure of overall patient health status are examples of other such outcomes.

Additional objects, features, and advantages of the various aspects of the present invention are included in the following description of its preferred embodiments, which description should be taken in conjunction with the accompanying drawings.

BRIEF DESCRIPTION OF THE DRAWINGS

The charts of FIGS. 1A–C illustrate the relative variations of components of healthcare before and after the present invention.

DESCRIPTION OF THE PREFERRED EMBODIMENTS

Figure 1:
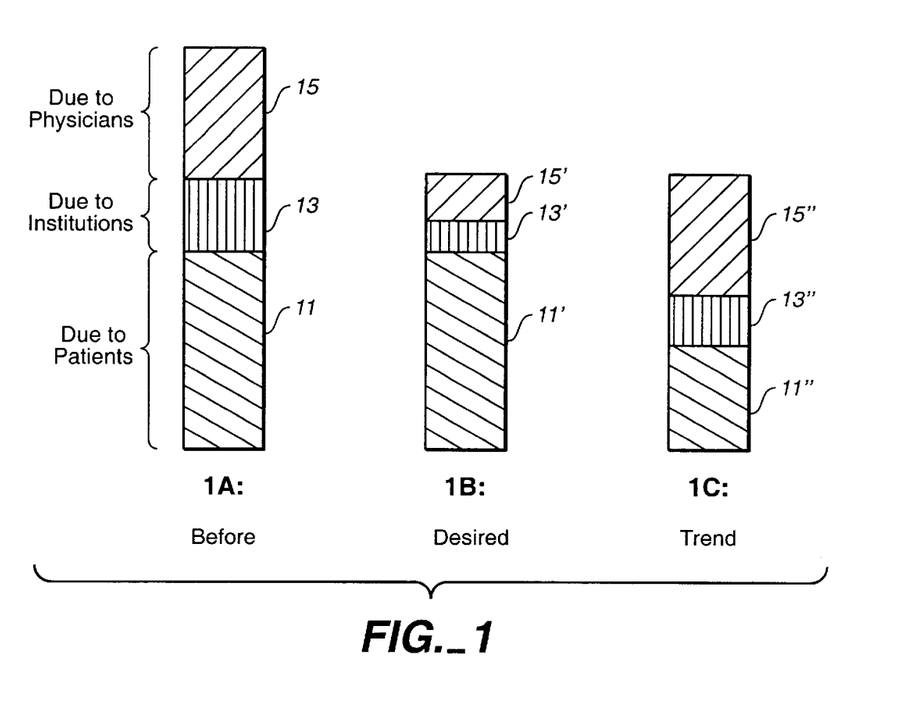

The three bar charts of FIG. 1 illustrate a primary goal of the present invention, compared with the effects of the current direction of healthcare management. Referring first to FIG. 1A, three components of variations in charges by healthcare providers for treating a particular primary illness among a population of patients are shown. One component 11 shows a theoretical proportion of the variation in charges that is inherent in a patient population. These charge variations are required to diagnose and treat the differences in clinical complexities of the patients in the group. Some patients are more clinically complex than others and therefore require a greater expenditure of healthcare resources. One patient may have a primary illness plus a secondary or collateral illness which causes the complexity and appropriate resource consumption to be greater. Another patient with the same age and primary illness that has no such other secondary or collateral condition will cost less to manage.

A component 13 of the bar chart of FIG. 1A indicates the portion of variation in charges that is due to differences in the operation of hospitals, clinics, laboratories and other institutions. One hospital, for example, may have patients who remain longer than in another hospital because of inefficiencies in discharge procedures, thus incurring greater charges for treating the same illness. A component 15 represents the variation in charges due to physicians. Some physicians order more laboratory tests, radiology, and the like, or require patients to return for more office visits, than others. The variations represented by the components 13 and 15 are desired to be minimized by effective management of healthcare institutions and physicians.

The bar chart of FIG. 1B illustrates a result of using the data processing techniques of the present invention. A component 11' of variations of charges to treat the group of patients with the same illness remains unchanged from the component of FIG. 1A. Indeed, this must be the case since variations in clinical complexities of the illnesses among the population of patients cannot be changed by statistical manipulation, and sicker patients cost more to treat properly. What can be controlled, without failing to give the sicker patients the care they need, is the variation among the institutions and physicians, as indicated by components 13' and 15' that are reduced versions of the variation components 13 and 15 of FIG. 1A. That is, the techniques of the present invention allow, for example, the identification of inefficient care processes and physicians who order too many laboratory tests, or not enough, when treating the same illness, after taking into account the complexity of the illnesses of the physicians' patients. This then allows management of the healthcare providers by establishing norms so physicians and institutions can improve care processes which caused their deviations from the norm for each of a large number of defined illnesses. The present invention allows the physician and institution variation components 13 and 15 to be identified and therefore appropriately reduced, as shown in FIG. 1B, as opposed to previous techniques that result in cost reductions that inappropriately reduce expenditures in the patient component 11, as shown in FIG. 1C.

The present invention provides an estimate of treating a particular patient, or group of patients, for a specific illness, or group of illnesses, that accurately accounts for differences in resource consumption (charges) due to varying levels of clinical complexity of the patients. As described below, this is done by forming an indexed data set from healthcare records of a large (at least several thousand) population of patients. A large table of linear regression coefficients is calculated from this indexed data set, one set of regression coefficients for each of several hundred defined illnesses, that takes into account related illnesses (co-morbidities), complications and other complicating factors. To form an estimate of charges to treat a particular patient for a given illness, the coefficients for the same illness are read from the table of regression coefficients and used in the same estimate model that was used to calculate them from the indexed data set. The resulting estimate will have small variations from the particular level of sickness of the patient (component 11') since that is taken into account. Any significant difference between such an estimate and the actual charges can then be attributed to the healthcare providers. This difference is valuable information that is then used to advise or manage the care processes of healthcare providers, resulting in the small components 13' and 15' of variation that are attributed to the providers.

Without the ability to identify the causes of variations in the costs needed to appropriately treat different patients with similar illnesses, the previous systems tend to reduce variations by considering that treatment of all patients with the same illness should cost about the same. The only exceptions to this include providing one or two separate sub-categories associated within a given illness for those patients who are elderly, have any co-morbidity or complication, and the like, based upon the resulting added cost to treat such patients. But this simply provides an average cost to treat all patients for a given illness, or perhaps one or two additional average costs for older patients and/or those who are sicker from some other illness. The added category for patients with a co-morbidity cannot take into account the wide spread in the amount of additional cost incurred to treat those patients having different one(s) of hundreds of possible secondary illnesses.

FIG. 1C illustrates a highly undesirable outcome of managed care initiatives which is the result of not having the capabilities of the present invention. The inappropriate racheting down of healthcare costs is occurring because the present health data is insufficiently risk adjusted and therefore unreliable. Payers and governmental agencies gather these unadjusted data and use them for the purpose of reimbursing, managing and evaluating healthcare providers. The limitation of this approach is that patients' clinical complexities are unquantified and therefore the appropriate numbers and types of treatment resources are unknown. This penalizes physicians and hospitals who manage the most difficult cases and ultimately withholds care from the neediest patients. As this illustration and recent history clearly demonstrate, when fewer total dollars are allocated for care, the variations of physicians and hospitals remain virtually the same, and the costs necessary to manage patients' clinical variations come largely out of the patient component in the form of withholding of care.

Thus, as shown in FIG. 1C, the total variation of estimates to treat a given illness will likely be reduced from the picture of FIG. 1A of the way it used to be. But this reduction in total variation is also causing an artificial reduction in a patient component 11", as well as in institution and physician components 13" and 15". The reduction in the patient component 11" can only mean that the sicker patients are not receiving the care they need, and/or those not so sick are receiving more care than they need. Adequate information is not being provided to healthcare providers from which they can improve their care processes. The present invention rectifies this fundamental deficiency.

Figure 2:
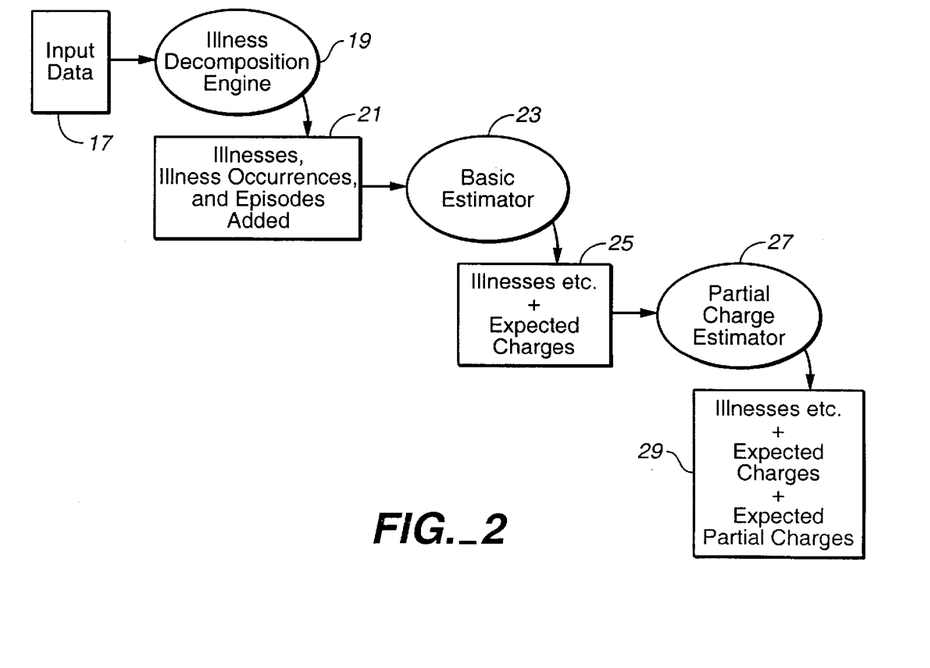
FIG. 2 shows the major stages of the data processing used to implement the present invention.

Referring to FIG. 2, the stages of data processing used to implement the present invention are outlined. As an input to the processing indicated at 17, data is provided of encounter records for a patient or patients whose expected charges are to be estimated. Data from these records are input into the computer system. These patient records include hospital discharge forms, insurance reimbursement forms, and similar sources of patient data. Data on these forms include identifying information of the patient, including gender and age, codes of a primary and any secondary diagnoses, codes of any procedures performed, both primary and secondary, any applicable DRGs, date(s) the services were provided, identifying information of the health provider and charges for providing the services.

The remaining stages of FIG. 2 are generally outlined, with added explanation being provided below. Input data 17 is decomposed in processing of a stage 19. The primary purpose of the stage 19 is to group the encounter records into episodes of care for identified primary and collateral illnesses. These results are indicated as an output 21. A next stage 23 estimates charges for various of these episodes and complete illnesses, adding the results of this processing to the output 21 of the decomposition stage 19, forming a more complete output 25. The processing can stop here but it is often desirable to include another processing stage 27 to calculate, from the results of the output 25, charges for various types of procedures. An output 29 includes the results of each of the processing stages 19, 23 and 27. These results include estimated charges for the patient or group of patients that can be compared with the actual charges or otherwise used in the management of a healthcare system.

Figure 3:
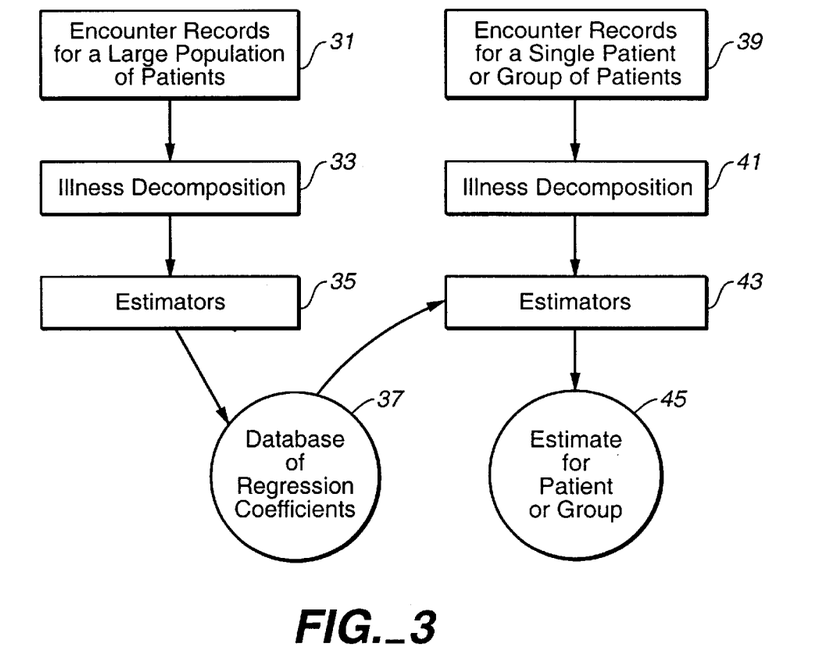
FIG. 3 outlines in a general way the procedures used to estimate healthcare charges.

Before explaining the steps of the estimation processing of FIG. 2 in more detail, reference is made to FIG. 3 wherein the same estimation processing is illustrated along with steps to form the table of regression coefficients upon which the estimations are dependent. The table is calculated from the indexed data set of healthcare encounter records of a large population of patients, such as exist with a large health insurance company, health plan of a large corporation, and similarly other sources. Generally, the larger the number of patients and the longer the period of time over which the encounters extend, the better. Data from such records is input into the computer in a step 31, followed by an illness decomposition step 33 and an estimating step 35. The algorithms used in the steps 33 and 35 are essentially the same as those of the steps 19 and 23 (and also preferably 27) of FIG. 2. Using the estimate models, regression analysis, such as least squares analysis, is used to calculate the regression coefficients. The result is a table 37 of regression coefficients for these estimate models. This table can be regularly updated by repeating the processing of the steps 33 and 35 on an enlarged volume of encounter records 31 that occurs over time.

When making an estimate of charges to treat a specific patient or group of patients (who will usually not be included in the population from which the encounter records 31 are taken), steps 39, 41 and 43 of FIG. 3 are performed, which correspond, respectively, to those of blocks 17, 19 and 23 (and also possibly 27) of the diagram of FIG. 2. In the estimation step 43 (corresponding to stages 23 and 27 of FIG. 2), appropriate ones of the regression coefficients are drawn from the database 37 for the primary illness(es) whose expected charges to treat are being estimated.

Returning to the estimation illustration of FIG. 2, an early step in the decomposition stage 19 is to identify a primary illness (denoted IL0) for each of the encounter records. This is done primarily from the diagnoses and procedure codes of the individual encounter records. ICD-9 or other types of codes, including DRGs if that is all that is shown on a record, are mapped into individual categories of an illness table. Up to nine secondary illnesses (IL1–IL9) are also identified for each encounter record, primarily from secondary diagnoses indicated on the patient record. These secondary illnesses, or "sub-illnesses", are primarily used later in the charge estimation stage, where their inclusion allows an accurate estimate to be made as to the risk of incurring expenses for an individual patient.

Another step in the decomposition stage is to gather the encounter records into records of episodes of care. Encounter records are grouped together according to certain rules concerning the duration of an individual episode. A primary illness and set of collateral illnesses are associated with each episode. For in-patient services (IP), a continuous stay in the hospital is considered to be a single episode. For office visits (OF), an episode is one day in length, as is a day encounter (DE) episode. A therapeutic series (TS) episode has a single length extending from the first to the last of a number of visits for therapy. If two or more episodes of different types that are created by these rules occur on the same day for the same illness, they are combined into a single episode that is given the type of the record having the highest priority. The episode types, in order of priority, are IP, TS, DE and OF. This usually results in the records having the lesser amount of charges being, in effect, folded into the one having the greater amount of charges.

Figure 5A:
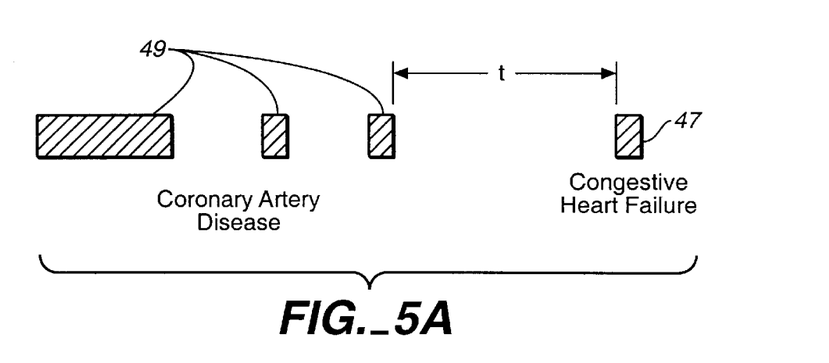
FIGS. 5A–B illustrate two time durations used in the illness decomposition portion of the present invention.

In assigning a primary illness to the episode records, the history of the patient for which the estimate is being made is utilized. The illness table makes such history relevant for certain of the illnesses mapped from the encounter records. An example of this is illustrated by FIG. 5A, wherein an episode is initially identified from the data on its encounter record(s) to be congestive heart failure. This is one of the illnesses in the illness table that is coded to be an illness itself, or an indication of some other illness, such as, in this example, coronary artery disease. For this type of initially mapped illness, the processing looks back in the same patient's records in order to determine whether an episode 49 of the higher level disease, in this case coronary artery disease, occurred within a time "t" before the current episode being evaluated. If so, the current episode is reclassified from the initially mapped illness to the higher level illness, in this case coronary artery disease. If not, the illness identified for the current episode remains that initially determined, in this case congestive heart failure.

In a specific form of the present invention, it is contemplated that estimates will be made for individual episodes of each type of care, namely IP, OF, DE and TS. Although this provides very useful information for managing the delivery of healthcare services, it has been found to be of even greater help to group episodes of care for the same primary illness over the length of that illness. In the case of acute illnesses, a broken arm being an example, the episodes of care extend over a predictable period of time. It is the cost of treating that entire occurrence of an acute illness that is useful to estimate for the purpose of comparison with the actual charges of the health providers. In this way, the delivery of services (care processes) to treat each illness across the entire continuum of care can be managed by the providers using process improvement techniques.

Figure 5B:
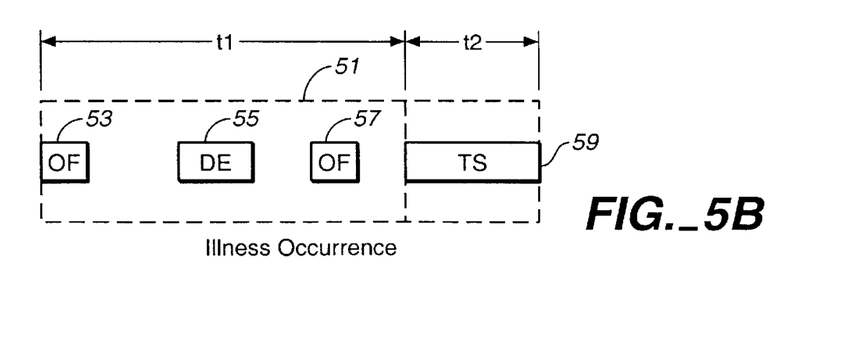

Each of the illnesses in the illness table that can be of an acute type is specified to last a certain time duration that is determined from experience for that illness. Such a duration "t1" is indicated for an illness occurrence 51 of FIG. 5B. This illness occurrence is shown to include several episodes of care 53, 55 and 57. The specified duration t1 commences with the first episode 53 for its primary illness. Any episodes occurring after time t1 will not be considered part of the same illness occurrence 51 but rather will begin a new one. An exception to this is in rather infrequent cases where an episode of that same illness has begun before the end of the period t1, in which case the duration of the illness occurrence is extended until the end of that episode. An example of this is shown in FIG. 5B, where another episode 59 of the same primary illness begins on the last day of the duration t1. The result is to extend the duration of this illness occurrence by a time "t2".

In addition to estimating charges for acute illnesses, charges are also estimated for chronic illnesses, diabetes being an example. Since chronic illnesses do not have a defined duration, but rather are indefinite in length, the cost is estimated per some unit of time, such as dollars per year, for providing care to a particular patient because of the chronic illness. By so estimating, a very useful comparison is made as to how various health providers take care of such illnesses.

Estimates of providing care for illness occurrences (acute) and illnesses (chronic) is preferably made of a combination of all forms of care, IP, OF, DE and TS. It has also been found useful, however, to make these estimates with only episodes of office visits (OF) and day encounters (DE). This reflects those services for which a primary care physician is usually responsible. Thus, the performance of primary care physicians can best be ascertained by such more limited illness and illness occurrence charge estimates.

Figure 4:
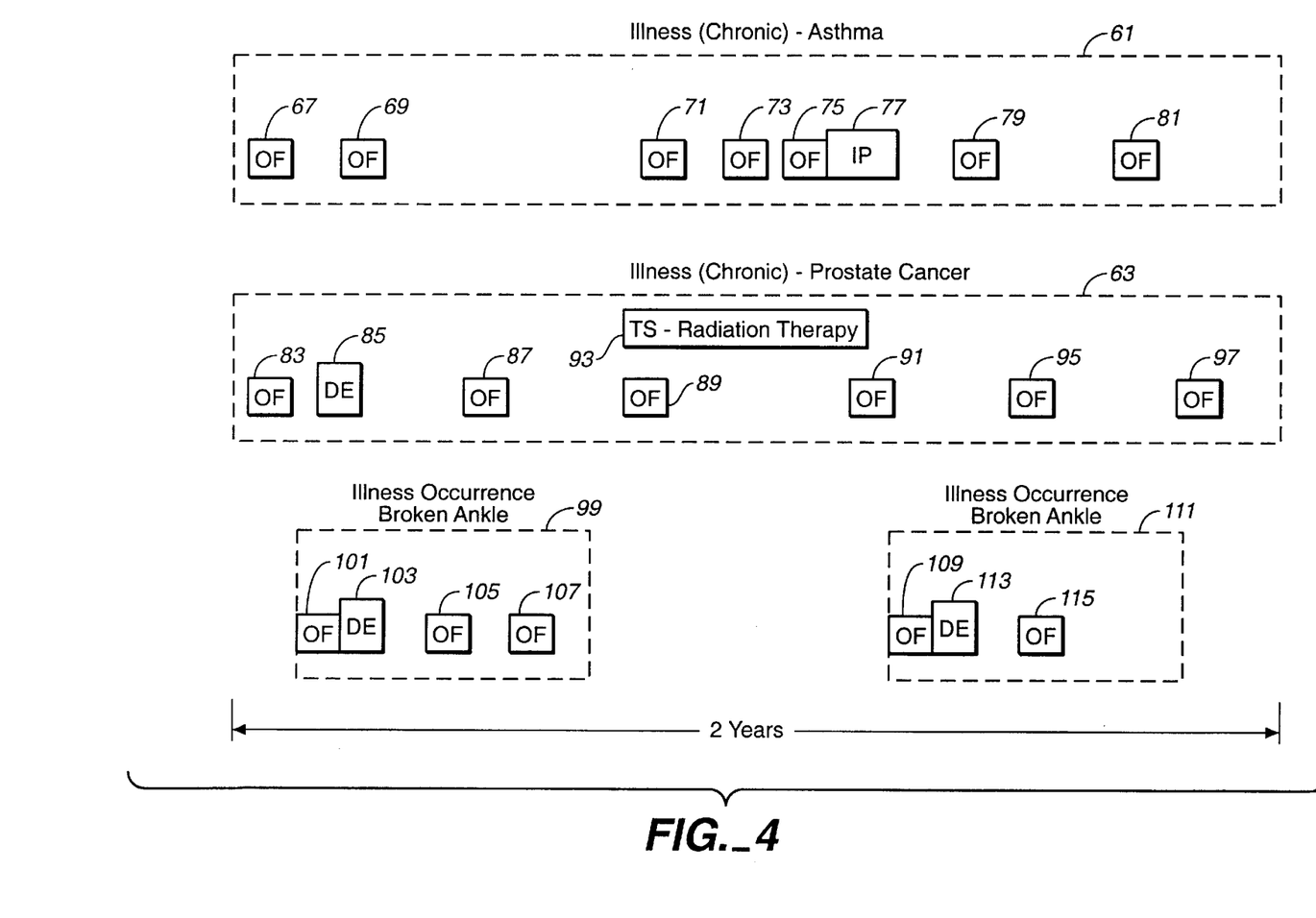
FIG. 4 shows an example of the illness decomposition processing for a single patient with multiple simultaneous illnesses.

An example of a single patient with multiple illnesses occurring at the same time is given in FIG. 4. Over the two year period shown, this hypothetical patient has two chronic illnesses, asthma 61 and prostate cancer 63. Treatment of asthma includes two office visits 67 and 69 for one flare-up of the illness. A subsequent flare-up of the asthma requires three office visits 71, 73 and 75, plus a hospitalization 77. Two post-hospitalization office visits 79 and 81 follow. The prostate cancer requires an office visit 83, a needle biopsy (day encounter) 85, and routine care office visits 89, 91, 95 and 97. A therapeutic series 93 provides radiation treatment for the cancer. Each of the boxes within the illnesses 61 and 63 is an episode of care for the respective illnesses. The therapeutic series episode 93 extends over some period of time during which the two office episodes 89 and 91 occur. If an office visit occurs on the same day as a therapeutic series visit or treatment, charges for this office visit will be included in the therapeutic series episode 93.

Further, during this same period the patient has an acute illness 99 of a broken ankle. This illness occurrence commences with an office visit 101, followed immediately by a day encounter 103 to place a cast on the ankle. Two follow-up office visits 105 and 107 end this occurrence of the illness, which has a finite duration defined in the illness table. Indeed, there is no further activity until much later when another office visit 109 takes place for a broken ankle again. This begins a second occurrence 111 of the same illness. Because the initial encounter 109 occurs after the close of the first illness occurrence 99, a new illness occurrence 111 is begun with this office visit. The initial office visit 109 is followed by a day encounter 113 and a follow-up office visit 115.

After completion of the decomposition stage 19 (FIG. 2), the patient encounter records have been decomposed into episodes, illnesses and illness occurrences. The present invention provides for estimating the charges for treating each of the illnesses 61, 63, 99 and 111, either with all the episodes of care shown or only with various combinations of them. This later option gives different results in each of the chronic illnesses 61 and 63 since the hospitalization and therapeutic series would not be included in the estimate.

Figure 6:
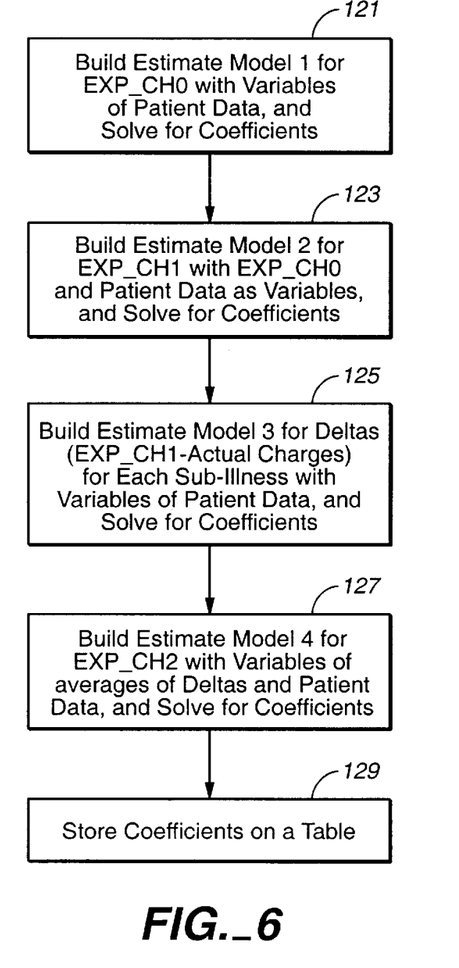
FIG. 6 is a general flow chart of the processing of patient data in order to form a table of regression coefficients.

The estimator stages 23 (FIG. 2), 35 and 43 (FIG. 3) use hierarchical linear regression analysis to estimate charges. A flowchart of FIG. 6 illustrates the processing of step 35 to generate the table of regression coefficients that are used in calculating expected charges. In a first step 121, an estimate model 1 is built by setting an initial rough estimate of charges EXP_CH0 equal to a sum of mathematical terms of variables and regression coefficients, such as, $$EXP\_CH0 = a_0 + a_1 x_1 + a_2 x_2 + \quad (1)$$

where $x_1$ and $x_2$ are model variables, and $a_0$, $a_1$, and $a_2$ are regression coefficients. The model variables are taken from the data of the large population of patients, the number of diagnoses (numdx) being an example of one variable "x". The EXP_CH0 is set to the actual charges incurred and the coefficients "a" are calculated for each value of one, or a combination of two or more, grouping variables taken from the patient encounter record data. This calculation is made by use of the least squares algorithm in order to find the coefficients "a" that cause equation (1) above to have the best fit with the data. An example of grouping variables is a combination of a primary diagnosis (dx0) and primary procedure (pr0) reported on the encounter records. That is, the coefficients "a" of equation (1) are calculated for each combination of "pr0" and "dx0" in the data of the patient population.

Instead of using a single estimate model with all the desired variables "x", and then solve for its many regression coefficients "a" for rather complicated numbers of combinations of grouping variables, two or more estimate models are used in order to make the processing easier and avoid having to simplify the estimate model to eliminate terms that are believed to be important to the estimate. Indeed, in one embodiment, equation (1) is reduced to only the first two terms. After the coefficients "a" of equation (1) are calculated in the manner described, that equation is used to calculate EXP_CH0 from the indexed patient data set. An estimate model 2 is then built, as indicated by a step 123 of FIG. 6, by using EXP_CH0 as a variable of the estimate model 2, $$EXP_{13}\ CH1 = b_0 + b_1\ (EXP_{13}\ CH0) + b_2 y_2 + b_3 y_3 + \quad (2)$$

where the regression coefficients are denoted by "b" and other variables by "y". The coefficients of this model 2 are solved by the least squares algorithm for each value of a grouping variable, or combination of two or more grouping variables, by setting EXP_CH1 equal to the actual charges. The calculated values of the coefficients "b" are then substituted back into equation (2) and EXP_CH1 is calculated for use in a third estimate model 125. Use of the estimate EXP_CH0, calculated by equation (1), as a variable in equation (2) makes the technique hierarchical.

Estimate model 3 solves for charge differences, or "deltas", for each sub-illness present in the patient data, thus directly correlating the estimates for treating a given primary illness with the concurrent existence of specific collateral illnesses (sub-illnesses). The estimate model 3 is, $$(EXP\_CH1 - \text{Actual Charges}) = c_0 + c_1 z_1 + c_2 z_2 + \quad (3)$$

where the regression coefficients are denoted by "c" and model variables by "z". The coefficients are calculated by use of equation (3) for each collateral illness. Thereafter, the coefficients are substituted back into equation (3) and delta charges (EXP_CH1—Actual Charges) are calculated.

A next and final step 127 of the regression analysis uses a linear regression equation (4) that equates a final estimate EXP_CH2 to a series of coefficients and variables. Various averages of the delta charges calculated in step 125 are used as model variables in equation (4). EXP_CH2 is set equal to the actual charges, and the coefficients of equation (4) calculated by least squares.

As a final step 129 of the flow chart of FIG. 6, all of the regression coefficients from steps 121, 123, 125 and 127 are stored in a table within the computer mass storage memory. This table is necessarily quite large since different values of the many coefficients of equations (1)–(4) have been determined for different values of grouping variables taken from the patient records. Also, there are a set of such coefficients by primary illness for each episode, illness and illness occurrence.

Figure 7:
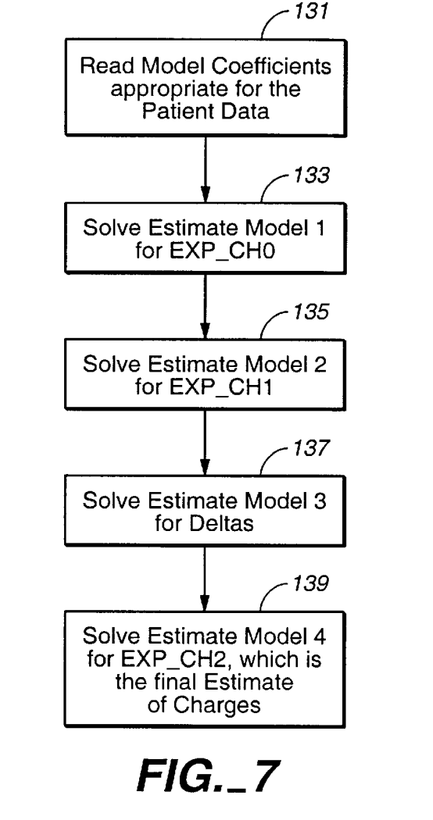
FIG. 7 is a general flow chart of the processing used to estimate charges.

Referring to the processing flow chart of FIG. 7, a first step 131 of determining expected charges for a given episode, illness or illness occurrence, as desired, for a given patient is to read from the coefficient table in memory those coefficients that are appropriate for the patient data. Since these are the coefficients used in each of the estimate models, they can also be read in conjunction with the use of those models.

As indicated by a step 133, the estimate model equation (1) is solved for EXP_CH0. Data of the given patient provide the model variables "x" of this equation, and a set of coefficients "a" is taken from the table formed in the step 129 as recited by the patient data. For example, if the coefficients were determined in the step 121 for each combination of a primary diagnosis (dx0) and primary procedure (pr0), then the coefficients determined for the specific combination of dx0 and pr0 existing in the subject patient's data are read from the stored table and substituted into equation (1).

Once EXP_CH0 is calculated, a next step 135 solves the estimate model equation (2) for EXP_CH1 by substituting actual data for the model variables "y" and choosing the coefficients "b" from the coefficient table that were determined for the specific grouping variables used in the step 123. Similarly, estimate model equations (3) and (4) are solved in respective steps 137 and 139. An expected charge EXP_CH2 is the result. This charge estimate is for an episode of care, illness, or illness occurrence, consistent with whether the patient data used and coefficients selected are for an episode, illness or illness occurrence.

It is desired to have the estimate models depend upon as much patient data as is available to provide the best results. But some patient records will not have some of the data that provides the best results. Rather than building a single estimate model for each of the models 1–4 that depends upon the least amount of patient data that is likely to be available most of the time, two or more alternative models are used for individual ones of the models 1–4. One of these models is made dependent upon data that gives the best results but may not always be available in sufficient quantities. A second of these models is made dependent upon a reduced amount or different patient data that is usually always available. The processing of each estimate model then uses the best of the two models for which patient data is available. This has the advantage of providing more accurate estimates than are possible with the patient data that is always available.

As an example, three alternative versions of the model equation (1) each have the number of diagnoses "numdx" as the variable $x_1$ but the regression analysis is performed in step 121 for three sets of grouping variables to result in three sets of coefficients that are stored in the table. The three sets of grouping variables are, in this example, a combination of the primary diagnosis (dx0) and primary procedure (pr0) for a patient, if they exist, a combination of pr0 and DRG, and the DRG alone. Use of the coefficients determined for each DRG alone to calculate EXP_CH0 gives results that are not as good as when one of the other versions of the model is used but the technique of using alternative models allows the most accurate result that is possible from the available data.

Figure 8:
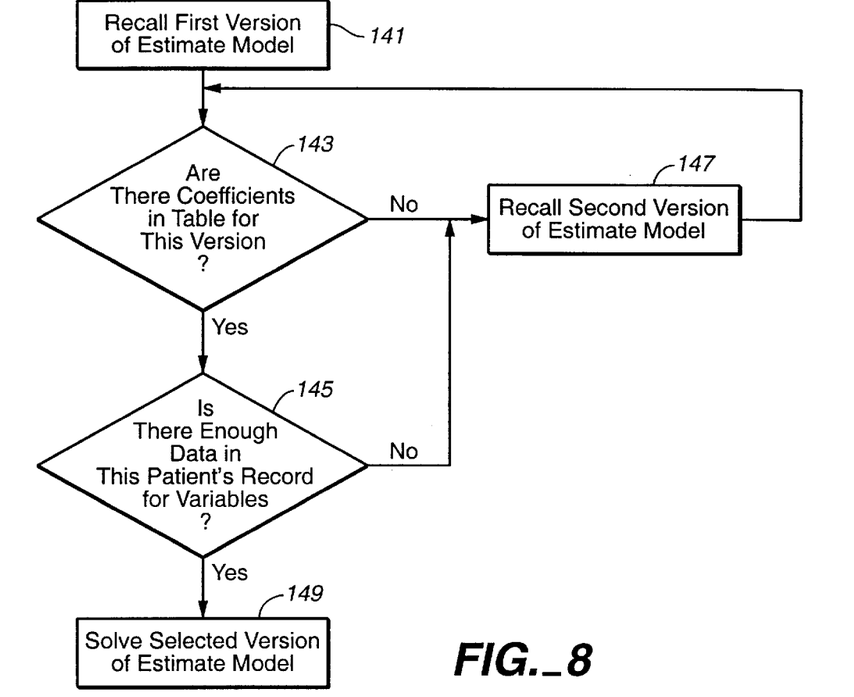
FIG. 8 is a flow chart illustrating the use of multiple alternative estimate models in the processing of either FIG. 6 or 7.

FIG. 8 illustrates the implementation of any of the steps 131, 133, 135 or 137 of FIG. 7 where two alternative versions of the estimate model are provided. In a step 141, a version of the model requiring the most data is recalled and a determination made in steps 143 and 145 whether there are coefficients in the table and enough data in the current patient record to use this version. If either the coefficients or the patient data is not available, a second version of the estimate model requiring less data is recalled, in a step 147, and the same tests of steps 143 and 145 made. The first one to pass the tests of the steps 143 and 145 becomes selected for use, as indicated in a step 149. Although use of only two alternative versions of an estimate model is shown, three or more can be employed if there is some advantage in doing so.

Figure 9:
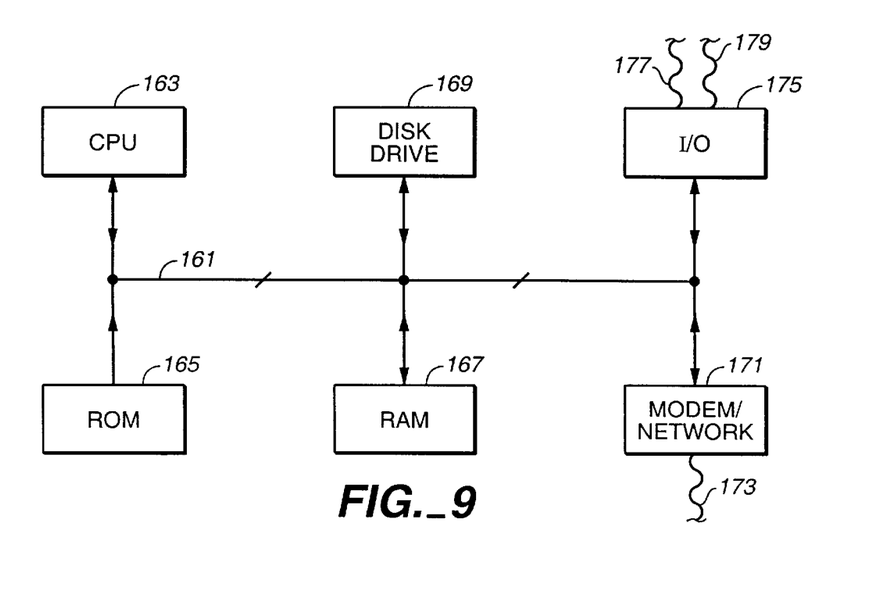
FIG. 9 illustrates, in block diagram form, a typical computer system used to carry out the processing illustrated in FIGS. 2–8.
Figure 10:
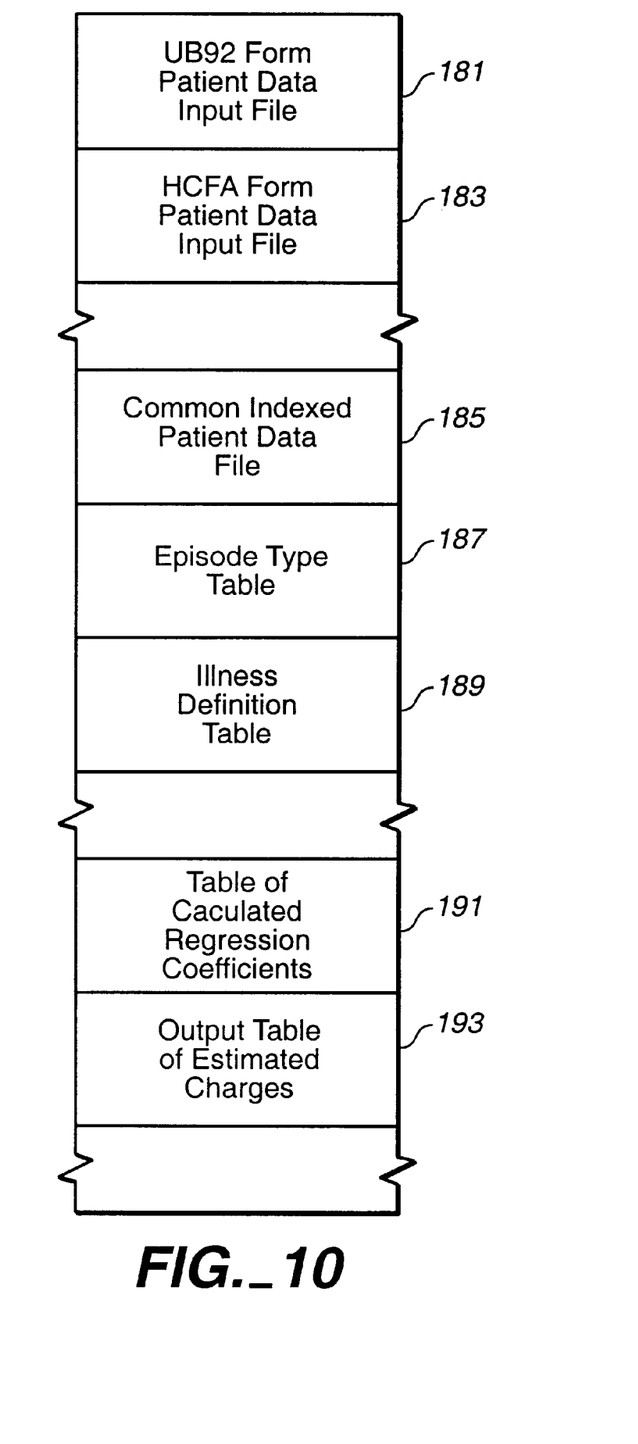
FIG. 10 schematically shows utilization of a memory of the computer system of FIG. 9.

An example of a computer system that may be used to carry out the foregoing processing is shown generally in FIGS. 9 and 10. FIG. 9 is a block diagram of the computer system hardware and FIG. 10 schematically shows a memory space within the computer system for storing various data files and tables. The hardware includes several functional units that communicate with each other over a common system bus 161. These units include a central processing unit (CPU) 163, a non-volatile read-only-memory (ROM) 165, a volatile random-access-memory (RAM) 167, and a magnetic disk drive mass data storage system 169. Also typically connected to the system bus 161 is a communications unit 171 that includes a modem and/or network interface to a circuit 173 that is a telephone line and/or a computer network connection. Another input/output unit 175 provides an interface between the bus 161 and at least two circuits 177 and 179 for connection with a keyboard, mouse, monitor, and other standard computer peripheral devices.

Several data files and tables are stored within the disk system 169 for reference by the CPU 163 during execution of various portions of the algorithm described herein. Some of the more important of these files and tables are shown in FIG. 10. Separate files are maintained for raw patient data in substantially the form received. Files 181 and 183 respectively store data from hospital discharge forms, such as UB92, and out patient charge records, such as HCFA 1500, and there will generally be several more in yet different formats. This raw input data is taken from these files, as part of the processing, and placed into a common file 185 in a common indexed format. It is the indexed data file 185 that is the source of patient data throughout the remaining processing. The file 185 is updated as the patient input data changes.

Two static tables 187 and 189 are utilized, but there can be more. The table 187 identifies, for medical code data from the indexed file 185, the type of the individual episodes of care. The table 189 defines illnesses and sub-illnesses for patient data from the file 185.

Another file 191 includes the calculated regression coefficients, so can change from time-to-time as the amount of patient data changes and at least some of the coefficients are recalculated. This file is accessed for individual ones of the regression coefficients as needed during the processing. A final file 193 illustrated in FIG. 10 stores the resultant calculated estimated charges. Additional files and tables can also be included as part of the processing system shown.

An example of an algorithm to implement the processing described herein is provided in a microfiche Appendix that is being filed with this application and forms a part of this description. The data files and tables of FIG. 10 are utilized in that algorithm.

Although the present invention has been described with respect to its preferred embodiments, it will be understood that it is entitled to protection within the full scope of the appended claims.

It is claimed:

1. A method of managing delivery of services by healthcare providers to medical patients, comprising:

(A) creating a table of regression coefficients from individual records of encounters of a population of patients with healthcare providers, by a method including:
    accumulating and storing data from the encounter records in a mass storage system of a computer, data of individual ones of the encounter records including at least (1) an identity of a single patient, (2) charges of the healthcare providers for the encounter, and (3) at least one diagnosis made or procedure performed,
    grouping said encounter records, from information provided therein, into a plurality of summary records for individual ones of the population of patients and one of a plurality of primary illnesses,
    establishing an estimate model of a total amount of charges for the encounters within a summary record as a function of a plurality of model variables and regression coefficients taken or derivable from the data within said summary records,
    solving, separately for individual ones of the primary illnesses, the estimate model for the regression coefficients that optimizes fits of said estimate model with the data within said summary records, and
    storing said regression coefficients in a table within the computer mass storage system, and (B) estimating the charges for treating an illness of at least one patient, by a method including:
    grouping, within the computer, data of the encounter records of said at least one patient, from information provided therein, into at least one summary record for one of the plurality of primary illnesses,
    reading the regression coefficients from said stored table for the primary illness of said summary record,
    solving the estimate model for estimated charges by use of the read regression coefficients, and (C) utilizing the estimated charges to manage the delivery of health services by the healthcare providers.

2. The method according to claim 1, wherein accumulating and storing records of individual encounters includes accumulating and storing records of hospital and outpatient encounters for individual patients, and wherein grouping the encounter records includes grouping records of hospital and outpatient encounters into common ones of the summary records.

3. The method according to claim 2, wherein the outpatient encounters for which data is accumulated, stored and grouped include office visits, day encounters and therapeutic services.

4. The method according to claim 1, wherein data of individual ones of the encounter records include data of patient conditions that are collateral to the primary illnesses, and wherein one or more of the model variables and/or regression coefficients of the estimate model is taken or derived from data of the collateral conditions.

5. The method according to claim 4, wherein data of collateral conditions includes data of illnesses other than the primary illness.

6. The method according to claim 1, wherein grouping said encounter records includes determining a primary illness for individual ones of the summary records.

7. The method according to claim 6, wherein determining a primary illness includes reviewing summary record data for an individual patient for data of encounters occurring prior to those for which data are included in the summary record.

8. The method according to claim 1, wherein establishing the estimate model includes establishing more than one specific estimate model with an estimate of charges of one specific estimate model being used as a model variable of a second estimate model, and wherein solving the estimate model includes solving the specific estimate models in sequence.

9. The method according to claim 8, wherein said one specific estimate model is chosen from multiple alternative specific estimate models that use a different set of model variables and/or regression coefficients from each other, and wherein solving the specific estimate model includes solving one of the multiple estimate models having the greater number of variables and/or regression coefficients for which encounter record data is available.

10. The method according to claim 1, wherein a length of time for which data of encounters is included in one of the summary records is specified for the primary illness of the summary record.

11. The method according to claim 10, wherein said length of time is an indefinite duration for chronic ones of the primary illnesses.

12. The method according to claim 10, wherein said length of time is a specified finite duration for acute ones of the primary illnesses.

13. The method according to claim 12, wherein said specified finite duration of time is extended when data exists of a succession of related encounters that begin within the specified duration but extend beyond said specified duration.

14. The method according to claim 1, wherein grouping data of the encounter records into the summary records includes first grouping such data into episodes of one of the plurality of primary illnesses and then grouping the data of the episodes into the summary records of the same primary illnesses.

15. The method according to claim 1, wherein the data of the encounter records of said at least one individual patient are not within the data from encounter records used to create the table of regression coefficients.

16. The method according to claim 1, wherein creating the table of regression coefficients and estimating the charges for treating an illness of at least one patient each include determining, from the summary records data and estimated charges, charges for one of a plurality of specific procedures performed.

17. A method of estimating charges of healthcare providers to at least one patient for the purpose of providing advice on the efficiency of such providers, comprising:

accumulating and storing, in a mass storage system of a computer, data from records of encounters of said at least one patient with healthcare providers that includes at least (1) an identity of said at least one patient, (2) charges of the healthcare providers for the encounter, and (3) at least one diagnosis made or procedure performed, grouping data of said encounter records, from information provided therein, into at least one summary record of said at least one patient for one of a plurality of primary illnesses, solving an estimate model of a total amount of charges for the encounters within a summary record as a function of a plurality of model variables and regression coefficients taken or derivable from the data within said at least one summary record, using regression coefficients previously determined with the same estimate model to optimize a fit of said estimate model for a population of patients with data within a summary record corresponding to said at least one summary record, and utilizing the estimated charges to advise on the efficiency of the healthcare providers in the delivery of health services.

18. A computer readable mass storage system storing the following:

a plurality of raw data files of individual records in multiple different formats of patient encounters with both in patient and out patient healthcare providers, a common patient data file containing an indexed version of the raw data contained in the patient encounter data files, a plurality of tables containing definitions including those of various illnesses, a table of regression coefficients calculated from at least the indexed patient data file and the definition tables for various combinations of primary and collateral illnesses, processing software including an estimate model that accesses the table of regression coefficients according to illnesses of specific patients to cause the computer to calculate from healthcare encounter data of such specific patients estimated charges to treat these patients, and an output table containing data of the calculated estimated charges.

19. A computer readable mass storage system storing the following:

a plurality of data files of individual records of patient encounters with both in patient and out patient healthcare providers, said records including patient illness diagnoses, a table of regression coefficients that have been calculated for various combinations of illnesses, processing software including an estimate model that accesses the table of regression coefficients according to illnesses of specific patients to cause the computer to calculate from healthcare encounter data of such specific patients estimated charges to treat those patients, and an output table containing data of the calculated estimated charges.

20. A method of estimating charges of healthcare providers to at least one patient, comprising:

accumulating and storing, in a mass storage system of a computer, data from records of encounters of said at least one patient with healthcare providers that includes at least (1) an identity of said at least one patient, (2) charges of the healthcare providers for the encounter, and (3) at least one diagnosis made or procedure performed, grouping data of said estimate encounter records, from information provided therein, into at least one summary record of said at least one patient for one of a plurality of primary illnesses, solving an estimate model of a total amount of charges for the encounters within a summary record as a function of a plurality of model variables and regression coefficients taken or derivable from the data within said at least one summary record, said regression coefficients having been previously determined with the same estimate model to optimize a fit of said estimate model for a population of patients with data within a summary record corresponding to said at least one summary record, and utilizing the estimated charges as an indication of the efficiency of the healthcare providers in the delivery of health services to said at least one patient.

21. The method according to claim 20, wherein accumulating and storing records of individual encounters includes accumulating and storing records of hospital and outpatient encounters for individual patients, and wherein grouping the encounter records includes grouping records of hospital and outpatient encounters into common ones of the summary records.

22. The method according to claim 21, wherein the outpatient encounters for which data is accumulated, stored and grouped include office visits, day encounters and therapeutic services.

23. The method according to claim 20, wherein data of individual ones of the encounter records include data of patient conditions that are collateral to the primary illnesses, and wherein one or more of the model variables and/or regression coefficients of the estimate model is taken or derived from data of the collateral conditions.

24. The method according to claim 23, wherein data of collateral conditions includes data of illnesses other than the primary illness.

25. The method according to claim 20, wherein grouping said encounter records includes determining a primary illness for individual ones of the summary records.

26. The method according to claim 25, wherein determining a primary illness includes reviewing summary record data for an individual patient for data of encounters occurring prior to those for which data are included in the summary record.

27. The method according to claim 20, wherein a length of time for which data of encounters is included in one of the summary records is specified for the primary illness of the summary record.

28. The method according to claim 27, wherein said length of time is an indefinite duration for chronic ones of the primary illnesses.

29. The method according to claim 27, wherein said length of time is a specified finite duration for acute ones of the primary illnesses.

30. The method according to claim 29, wherein said specified finite duration of time is extended when data exists of a succession of related encounters that begin within the specified duration but extend beyond said specified duration.

31. The method according to claim 20, wherein grouping data of the encounter records into the summary records includes first grouping such data into episodes of one of the plurality of primary illnesses and then grouping the data of the episodes into the summary records of the same primary illnesses.

* * * * *